(12) United States Patent
Kitcherside et al.

(10) Patent No.: US 8,388,911 B2
(45) Date of Patent: *Mar. 5, 2013

(54) FILTRATION CONTAINER

(75) Inventors: Michael Arthur Kitcherside, Congresbury (GB); Margaret Joan Kitcherside, Congresbury (GB)

(73) Assignee: Foss Analytical AB, Hoganas (SE)

( * ) Notice: Subject to any disclaimer, the term of this patent is extended or adjusted under 35 U.S.C. 154(b) by 399 days.

This patent is subject to a terminal disclaimer.

(21) Appl. No.: 12/831,163

(22) Filed: Jul. 6, 2010

(65) Prior Publication Data

US 2010/0272613 A1  Oct. 28, 2010

Related U.S. Application Data

(63) Continuation of application No. 10/399,371, filed on Apr. 16, 2003, now Pat. No. 7,807,466.

(30) Foreign Application Priority Data

Oct. 16, 2000 (GB) .................................. 0025315.3

(51) Int. Cl.
*B01L 3/00* (2006.01)

(52) U.S. Cl. ........ 422/527; 422/547; 422/549; 422/550; 422/534; 422/535; 210/321.67; 210/359

(58) Field of Classification Search ................. 210/297, 210/321.67, 350, 241, 359, 390, 399
See application file for complete search history.

(56) References Cited

U.S. PATENT DOCUMENTS

| | | | |
|---|---|---|---|
| 3,494,863 A | | 2/1970 | Greenman |
| 3,827,562 A | * | 8/1974 | Esmond ........................ 210/304 |
| 3,865,548 A | * | 2/1975 | Padawer ........................ 436/165 |
| 4,213,863 A | | 7/1980 | Anderson |
| 4,268,279 A | | 5/1981 | Shindo et al. |
| 4,592,849 A | | 6/1986 | McMillen |
| 4,753,889 A | | 6/1988 | Collins |
| 5,354,262 A | | 10/1994 | Boehringer et al. |
| 5,518,610 A | | 5/1996 | Pierpoline |
| 5,665,602 A | | 9/1997 | Caviezel |
| 5,782,383 A | | 7/1998 | Robinson |
| 5,888,399 A | | 3/1999 | Rutledge et al. |
| 6,184,039 B1 | | 2/2001 | Komarek et al. |
| 6,221,655 B1 | * | 4/2001 | Fung et al. ................. 435/288.1 |

(Continued)

FOREIGN PATENT DOCUMENTS

| | | |
|---|---|---|
| DE | 2001857 | 1/1970 |
| JP | 9-189699 | 7/1997 |

(Continued)

OTHER PUBLICATIONS http://www.thefreedictionary.com/fat, 2010.

(Continued)

*Primary Examiner* — Yelena G Gakh
*Assistant Examiner* — Christopher A Hixson
(74) *Attorney, Agent, or Firm* — Christie, Parker & Hale, LLP

(57) ABSTRACT

A filtration container (1) includes a container body (2) including a porous filter (4) exhibiting both hydrophilic and oleophobic properties. The container also has a lid (3) which provides a secondary filter for the container (1). The filter is slidable within the container body and is rotatable into a vertical position. The filtration container may be used for testing a fat content of an item placed within the container. A method for testing the fat content of an item is also provided.

26 Claims, 1 Drawing Sheet

U.S. PATENT DOCUMENTS 6,357,602 B2  3/2002  Rutledge et al.
6,472,036 B2  10/2002  Saint-Ramon et al.

FOREIGN PATENT DOCUMENTS

JP  10-288571  10/1998
WO  WO 99/02959  1/1999

OTHER PUBLICATIONS htttp://http.filtsep.com/latest_features/feature_articles/20060602_medical_filtration_devices.html, 2010.

http://www.wmich.edu/ppse/Offset/pp8.htm , 2010.

* cited by examiner

FILTRATION CONTAINER

CROSS-REFERENCED TO RELATED APPLICATION(S)

This application is a continuation of U.S. patent application Ser. No. 10/399,371, which is a National Phase Patent Application of International Application Number PCT/GB01/04596, filed on Oct. 15, 2001, which claims the benefit of the filing date of GB 0025315.3, filed Oct. 16, 2000.

FIELD OF THE INVENTION

The present invention relates to a filtration container and a method of testing the fat content of an item.

BACKGROUND

There are many situations where it is desirable to perform a composition analysis of a material and test procedures for determining the composition of a material may require several processing steps where the reagent used in one step must be thoroughly removed from the container before advancing to the next step of the test. For example, it may be desired to find the total fat content (also referred to as the Oil B content) of a foodstuff. An established conventional laboratory technique (ISO 6492:1999) for doing this is to place a known weight of a food or foodstuff into a cellulose thimble. The food or foodstuff may then be treated with a solvent under reflux conditions in order to remove the unbound fat therein and collected in a pre-dried and weighed receptacle.

The next step in the process is to release bound fat from the material. This is achieved using a process wherein the solvent-treated material is quantitatively transferred to a flask and gently boiled with an acid of known concentration for a period of 60 minutes under reflux conditions, cooled to ambient temperature and a filtration aid added and mixed.

The contents of the flask are quantitatively transferred and filtered through double moistened filter papers of a pre-determined porosity and washed with distilled water until all the acid is removed. The residue remaining is oven dried for a period of 4 hours, removed from the oven, cooled and quantitatively returned to the thimble.

The next step in the process is to remove the unbound fat from the residue and this is achieved by subjecting the residue contained within the thimble to a second treatment with solvent under reflux conditions for a period of 5 hours, collecting the fat in a pre-dried and weighed receptacle.

The solvent is removed from the receptacle by evaporation, thus leaving the fat behind.

The receptacle containing the fat is dried and weighed in order to determine the total weight of fat removed from the two treatments with solvent under reflux conditions.

The above process is labor intensive and time-consuming, allowing only one test per flask to be performed. The act of transferring the residue from the thimble to the flask for hydrolysis may result in leaving some of the residue behind. During the transfer of the hydrolyzed residue during the filtration process, some of the fat may be left behind. Fat may also be left behind on the reflux vessel, resulting in the loss of wanted constituents.

As prior art, there may also be mentioned WO99/02959.

SUMMARY OF THE INVENTION

According to a first aspect of the present invention, there is provided a filtration container comprising a container body including a porous filter exhibiting both hydrophilic and oleophobic properties, having for example the ability to retain fat in a hydrolysis step and release it during a solvent extraction step.

The filtration container may be provided with a closure for the container body, which closure may mechanically engage with the container body so as to secure the closure to close the container body at one end, for example being held in a push fit engagement with the container body.

The closure may also provide a secondary filter for the container, for example being domed to increase the surface area of the secondary filter.

The porous filter may be slidable in the container body and expandable and/or rotatable.

The container body could be rigid.

The container body could be substantially cylindrical.

The container body may comprise a polymer (such as polypropylene or polytetrafluorethylene (PTFE)) or glass.

The porous filter may comprise a polymer, for example a polyester.

The closure could comprise glass fibers or cellulose or a porous polymer or a sintered material to provide such a secondary filter.

According to a second aspect of the present invention, there is provided a method of testing a fat content of an item, comprising the steps of placing the item within a filtration container and then performing one or more of the following steps.

1. solvent extraction of fat and re-weighing the container;
2. using a liquid to separate bound fat and removing the liquid and soluble components from the container and, optionally, re-weighing;
3. washing in water, removing the water soluble components from the container and, optionally re-weighing the container;
4. drying the container to remove moisture and weighing the container;
5. solvent extraction from the container and optionally weighing the receiving receptacle; and
6. burning the container to remove organic matter within the container and weighing.

According to a third aspect of the present invention, there is provided a filtration container comprising a body containing an internal filtration membrane which retains fats during hydrolysis and washing procedures, with an additional external filtration membrane which is added prior to a solvent extraction procedure.

It is thus possible to provide a container which allows removal of fats pre-hydrolysis (optional) and post hydrolysis without losses of fat. Comparative data between the conventional method (ISO 6492:1999) and a method according to the invention has shown that when using the latter, the initial solvent extraction step is unnecessary, thus saving substantial time.

Preferably, the container has a closure, such as a lid, such that the sample can be placed in the container and sealed therein prior to the analysis. The closure may be held in a push fit engagement with the container. Alternatively, the closure may be securely engaged with the container, for example by means of co-operating screw thread portions or some other mechanical engagement mechanism.

Advantageously, a surface of the removable lid comprises a suitable membrane to provide such an external filtration membrane used during the solvent refluxing processes.

The inventors have found that certain materials such as glass fibres or cellulose or a sintered material are suitable for the external filtration membrane of the lid due to its temperature and chemical resistance.

Preferably the container is rigid and constructed of a material capable of withstanding high temperatures and also exhibiting chemical resistance. Advantageously, the body of the container should also exhibit non-stick properties and the inventors have found that a polymer (such as polypropylene or PTFE) or glass is suitable for this application.

The internal filtration membrane should be able to be repositioned post hydrolysis, thus allowing rapid removal of water and elimination of condensation during drying. It should exhibit hydrophilic and also oleophobic properties to allow rapid transmission of acid and water during a hydrolysis process but to retain hydrolized fats within the container during emptying and washing procedures following hydrolysis. Following drying, the filter should exhibit the ability to be able to be rotated to a vertical position prior to the final solvent extraction, to get a more rapid extraction. The inventors have found that a spiral construction using a polyester material enhances the hydrophilic nature of the internal filtration membrane and also allows the surface area of the membrane to be substantially increased post acid hydrolysis, which increases its hydrophilic properties and increases the speed of drying the residue and membrane prior to final solvent extraction.

It has also been found that rotation of the internal membrane prior to the final solvent extraction improves the efficiency of the removal of total fats.

The external, detachable filtration membrane, which as stated above, is advantageously part of a lid, which is initially used to contain the sample under test, must be capable of only allowing the passage of fats solubilized within the solvent (for example petroleum ether) to pass through it.

According to a fourth aspect of the present invention, there is provided a method of testing a fat content within an item, comprising placing the item within a container and then performing one or more of the following steps:
1. solvent extraction of fat, removal of solvent from a receiving vessel, and drying and re-weighing the receiving vessel;
2. using a liquid to separate bound fat and then removing the liquid and washing with distilled water;
3. drying the residue in an oven and optionally re-weighing; and
4. solvent extracting the hydrolysed residue, removal of the solvent from the receiving vessel and drying and re-weighing the receiving vessel.

BRIEF DESCRIPTION OF THE DRAWINGS

The present invention will now be described, by way of example, with reference to the accompanying drawing in which.

DETAILED DESCRIPTION OF THE INVENTION

Figure 1:
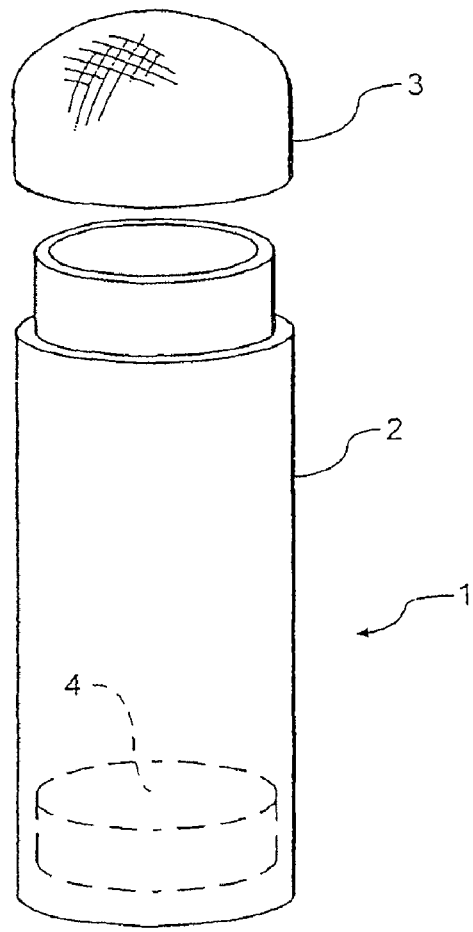
FIG. 1 is a perspective view of a container according to an embodiment of the present invention.
Figure 2:
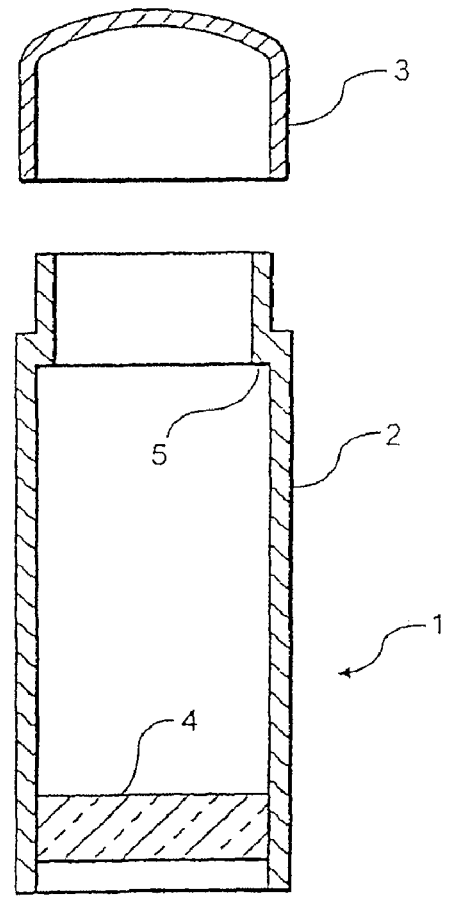
FIG. 2 is a longitudinal sectional view of the container.

A container 1 illustrated in FIGS. 1 and 2 comprises a rigid cylindrical container body 2 comprising glass or a polymer such as polypropylene. The container body 2 is provided with a lid 3 which comprises a porous cellulose dome which engages with the container body 2 allowing only soluble components to pass through it. The domed shape is designed to increase the surface area of the filter, thus allowing more effective solvent extraction.

The lid 3 has a dual purpose, firstly to contain test material in the container 1 prior to analysis and secondly to separate the soluble components from insoluble components during solvent extraction.

The container body 2 contains a porous filter 4, the preferred design being a spirally wound expandable, slidable and rotatable polyester filter (acting as a filtration membrane) which exhibits hydrophilic and also oleophobic properties, this not only enhancing the drying process post hydrolysis but also the final solvent extraction. Inside the container body 2 there is an internal shoulder 5, acting as a stop when the filter 4 is moved towards the lid 3 (see below).

In use, a sample (not shown) is introduced into the container body 2. The lid 3 is affixed to the container 1, thus trapping the sample therein and the container is re-weighed to obtain the weight of the sample.

If the sample is a food or feed product and it is desired to determine its total fat content, a weight of the food product is placed in the container 1. The sample then undergoes a hydrolysis process, which releases the bound fat, in the absence of the lid 3.

At completion of this stage, the water soluble phase is separated by filtration, draining out of the container body 2, leaving behind the fats, oils and waxes and non-hydrolyzed material, which remain within the container body 2. The porous nature of the filter 4 retains the hydrolyzed fats, oils and waxes and hydrolyzed material within the container body 2.

After the step of hydrolysis, e.g. by boiling in acid, has been completed, the container body 2 may be flushed with distilled water until the material contained within the container body 2 is free of acid. Prior to solvent extraction, it is necessary to remove the water from the hydrolyzed sample and filter 4, and this is achieved by sliding and expanding the filter 4 to its upper position against the shoulder 5 using a tool provided. The inventors have found that this process speeds up the drying procedure by increasing the surface area of the sample and filter 4 and reduces condensation. For this purpose, the bottom of the container body 2 may be open as shown or shaped to receive an appropriate tool.

Next, the container body 2 and its contents may be oven dried, e.g. in a microwave oven, prior to the final stage of solvent extraction.

Prior to the final solvent extraction, the filter 4 is rotated to a vertical position, this enhancing efficient solvent extraction, and the lid 3 is put in place on the container body 2.

Fats, oils and waxes (the crude (or total) fat) of the sample are removed from the hydrolyzed material by subjecting the container and its contents to solvent extraction, the fats, oils and waxes being solubilized and collected in a pre-dried and weighed receiving receptacle which is finally dried and re-weighed. The increase in weight of the receptacle represents the total weight of fats, oils and waxes contained within the material and called in the art Oil B.

Table 1 shows various determinations of Oil B in various materials. Each material was tested using the conventional prior art method described above and a method according to the invention, using the above-described container. The results for the prior art Oil B method, and the method using the invention are each presented in columns, the left-hand column in each case containing experimental results, and the right-hand column containing the averages.

TABLE 2

ALL DATA IS EXPRESSED IN gms/100 gms

| MATERIAL | PRIOR ART | THE INVENTION |
|---|---|---|
| WHEY | 0.81 | 0.81 |
|  | 0.89 (0.85) | 0.87 (0.84) |
| OATS | 8.84 | 8.58 |
|  | 9.21 (9.03) | 8.42 (8.50) |
| DRINKING CHOCOLATE | 12.60 | 12.77 |
|  | 12.92 (12.76) | 12.84 (12.81) |
| DRIED YOGURT | 10.00 | 10.34 |
|  | 9.91 (9.96) | 10.23 (10.29) |
| DRIED MILK | 25.27 | 25.69 |
|  | 25.88 (25.58) | 25.86 (25.78) |
| SUET | 78.43 | 79.68 |
|  | 79.88 (79.16) | 79.75 (79.72) |
| SKIMMED MILK | 0.79 | 0.99 |
|  | 0.69 (0.74) | 0.74 (0.87) |
| FULL FAT SOYA | 20.32 | 20.11 |
|  | 20.39 (20.36) | 20.19 (20.15) |
| FISH MEAL | 12.11 | 11.42 |
|  | 12.16 (12.14) | 11.64 (11.53) |
| WHEAT | 2.22 | 2.18 |
|  | 2.21 (2.22) | 2.06 (2.12) |
| BISCUIT MEAL | 14.83 | 15.18 |
|  | 14.86 (14.85) | 15.09 (15.14) |
| SEMOLINA | 1.58 | 1.56 |
|  | 1.49 (1.54) | 1.56 (1.56) |
| MAIZE | 4.73 | 4.98 |
|  | 4.98 (4.86) | 4.99 (4.99) |
| GRASS | 1.11 | 1.42 |
|  | 1.25 (1.18) | 1.31 (1.37) |

As can be seen from the conventional prior art method, dried milk gave a mean value of 25.58 gms per 100 gms of sample with a range of 0.43. The use of the present invention gave a mean value of 25.78 with a range of 0.12. In general the use of the invention gave greater agreement between replicates than the conventional prior art method.

It is thus possible to provide a filtration container for analytical use which functions both as a container and a filter element. This enables the transfer of materials to be eliminated, thereby giving an increase to experimental accuracy. The use of container 1 also increases the capability of a laboratory to perform many tests simultaneously.

The container 1 may, in use, be held within a rack or carousel assembly which aids the placement and removal of one or more containers into and out of beakers containing reagents used in the analysis.

The container may be used to perform a number of tests. An example of a test for the Oil B content of a food is described below:

1. For each test, weigh 1.5-2.0 grams of a sample into a container body 2 and place the container 1 into a carousel which can take several samples (e.g. 6).
2. If required, independently determine the dry matter content of each material using a standard oven drying method.
3. Measure out 350 mls of Hydrochloric Acid (3 molar) and transfer to a first extraction beaker.
4. Lower the carousel gently into the beaker of solution and moisten the surface of each sample with acid using a disposable pipette.
5. Place the beaker on a pre-heated hotplate, replace the condenser and bring to a gentle boil under reflux conditions. This procedure is repeated for each set of tests.
6. After 1 hour from the point of boiling, remove the beaker from the hotplate, cool to ambient temperature and remove the carousel from the beaker and allow the containers 1 to drain.
7. Discard the acid and solubles within the beaker and fill with purified water at ambient temperature. Lower the carousel into the water, ensuring all the containers refill. Remove the carousel and drain the containers and beaker and repeat until the washes become neutral, which may be tested with pH test paper.
8. All drained containers are placed for a few minutes on tissue paper to remove excess water.
9. Using the tool provided, the internal filter 4 of each container 1 is expanded and repositioned to its uppermost limit.
10. The containers containing the residues are oven dried to a constant weight in a microwave oven to remove the water.
11. A filter lid 3 is fitted to each container 1, a small plug of cotton wool inserted to retain the sample and each placed in a solvent extraction assembly and refluxed for a specific period. The fats, oils and waxes are collected within a pre-dried and weighed receptacle.
12. Finally, the solvent is removed from each receptacle, placed in a rack and oven dried (100° C.) to a constant weight and re-weighed. The increase in weight is reported as Oil B.

The Oil B content can be calculated from the following equation:

$$\% \text{ Oil } B \text{ in the Dry Matter} = \frac{\text{Flask} + \text{Oil } B \text{ Weight} - \text{Flask Weight}}{\text{Sample Weight} \times \text{Dry matter grams/gram}} \times \frac{100}{1}.$$

What is claimed is:

1. A filtration container for use in measuring the fat content of an item comprising:
   a container body configured for retaining an item the fat content of which is to be analyzed by hydrolysis, wherein the container body is formed with solid side walls; and
   a porous filter which is constructed to allow the transmission of water therethrough while retaining fat and oil within the container body,
   wherein the porous filter is contained within the container body in abutment about its periphery with the solid side walls thereof and slidable therein between a first position at which the filter defines in cooperation with the solid side walls a first container volume and a second position at which the filter defines in cooperation with the solid side walls a second container volume, and
   wherein, in both the first and second positions of the filter, the filter allows a passage of water from the respective first or second container volume through the filter, and
   wherein in the second position of the filter, the filter is rotatable with respect to the container body to a vertical position,
   wherein the filter closes an open bottom end of the container body, and
   further comprising a lid that closes an open top end of the container body, the lid providing a secondary filter for the container body.

2. A filtration container according to claim 1, in which the lid mechanically engages with the container body so as to secure the lid to close the container body at the top end.

3. A filtration container according to claim 2, in which the lid is held in a push fit engagement with the container body.

4. A filtration container according to claim 1, wherein the secondary filter is configured to allow transmission of solubilized fats and prevent transmission of insoluble fats.

5. A filtration container according to claim 4, in which the lid is domed to increase the surface area of the secondary filter.

6. A filtration container according claim 1 in which the porous filter is expandable.

7. A filtration container according to claim 6, wherein the porous filter is spiral wound.

8. A filtration container according to claim 1, in which the container body is rigid.

9. A filtration container according to claim 1, in which the container body is substantially cylindrical.

10. A filtration container according to claim 1, in which the container body comprises a polymer or glass.

11. A filtration container according to claim 1, wherein the porous filter comprises a polymer.

12. A filtration container according to claim 11, in which the polymer is a polyester.

13. A filtration container according to claim 4, wherein the closure comprises glass fibers or cellulose or a porous polymer or a sintered material to provide the secondary filter.

14. A filtration container according to claim 1, provided with an internal step which retains the filter in the second position.

15. A filtration container according to claim 14, in which the internal step is in the form of an internal shoulder on the solid side walls of the container body.

16. A filtration container according to claim 1, wherein the filter comprises first and second opposite sides, on opposite sides of the periphery of the filter, and wherein the first and second sides are slidable with the filter to the first and second positions.

17. A filtration container according to claim 1, wherein, in both positions of the filter, the filter is in fluid communication with first and second opposite ends of the container.

18. A filtration container according to claim 1, wherein a lower container volume opposite the filter from the first and second container volumes changes when the filter is slidable from the first position to the second position.

19. A filtration container for use in measuring the fat content of an item comprising:
a container for retaining an item the fat content of which is to be analyzed by hydrolysis, wherein the container is formed with solid side walls; and
filter means for allowing the transmission of water therethrough while substantially preventing the transmission of fat and oil,
wherein the filter means is contained within the container and is slidable therein between a first position at which the filter means defines in cooperation with the solid side walls a first container volume and a second position at which the filter means defines in cooperation with the solid side walls a second container volume, and
wherein in the second position, the filter means is rotatable with respect to the container to a vertical position.

20. A filtration container according to claim 19, further comprising a lid having secondary filter means, the lid closing an open top end of the container.

21. A filtration container for use in measuring the fat content of an item, comprising:
a container body formed with solid side walls;
a porous filter constructed to allow the transmission of water therethrough while retaining fat and oil within the container body; and
an item with a fat content that is to be measured, the item being retained by the container body and the filter,
wherein the porous filter is contained within the container body in abutment about its periphery with the solid side walls thereof and slidable therein between a first position at which the filter defines in cooperation with the solid side walls a first container volume and a second position at which the filter defines in cooperation with the solid side walls a second container volume,
wherein the filter closes an open bottom end of the container,
wherein the solid side walls comprise an internal step opposite the open bottom end, wherein the step retains the filter in the second position, and
wherein in the second position of the filter, the filter is rotatable with respect to the container body to a vertical position.

22. The filtration container of claim 21, further comprising a lid closing an open top end of the container, the lid comprising a second filter.

23. The filtration container of claim 20, wherein the filter means closes an open bottom end of the container.

24. The filtration container of claim 15, wherein the internal step is narrower than the open bottom end of the container.

25. The filtration container of claim 1, wherein the open top end is narrower than the open bottom end of the container.

26. The filtration container of claim 1, wherein the open bottom end is as wide as the filter.

* * * * *